(12) United States Patent
Rae

(10) Patent No.: US 7,294,838 B2
(45) Date of Patent: Nov. 13, 2007

(54) TRAVERSING MEASUREMENT SYSTEM FOR A DRYER AND ASSOCIATED METHOD

(76) Inventor: Todd A. Rae, 5106 Buttermilk Rd., Pylesville, MD (US) 21132

( * ) Notice: Subject to any disclaimer, the term of this patent is extended or adjusted under 35 U.S.C. 154(b) by 415 days.

(21) Appl. No.: 10/494,017

(22) PCT Filed: Oct. 30, 2002

(86) PCT No.: PCT/US02/34695

§ 371 (c)(1),
(2), (4) Date: Apr. 29, 2004

(87) PCT Pub. No.: WO03/037111

PCT Pub. Date: May 8, 2003

(65) Prior Publication Data

US 2005/0011528 A1   Jan. 20, 2005

(51) Int. Cl.
*G01J 5/02* (2006.01)
(52) U.S. Cl. .................................. 250/339.1
(58) Field of Classification Search ............... 250/250, 250/339.1
See application file for complete search history.

(56) References Cited

U.S. PATENT DOCUMENTS 4,971,077 A   11/1990   Dominguez et al.
5,163,454 A * 11/1992   Clemons .................... 131/302
5,476,108 A   12/1995   Dominguez et al.
5,489,980 A    2/1996   Anthony
5,697,385 A   12/1997   Seymour et al.

OTHER PUBLICATIONS

Intelligent Measurement Solutions Tobacco Industry "TM710 Tobacco", Quality2Process, Inc.—product description.*
Vis/NIR Spectrometers "QualitySpec(R) iP Process Analytical System", Analytical Spectral Devices, Inc.—product description.*
NIR Technology "Moisttech", Moisttech On Line Moisture NIR sensor, NIR Technology—product description.*

* cited by examiner

Primary Examiner—David Porta
Assistant Examiner—Mark R Gaworecki
(74) Attorney, Agent, or Firm—John Kerins

(57) ABSTRACT

A system and method for obtaining measurements across a width of material being processed is provided, which includes a near-infrared (NIR) detector head (102) which reads and transmits an NIR signal that has been reflected from the material, and a fiber-optic cable (106) through which the signal is transmitted to a processor located remotely from the material being processed. A moisture level reading can be obtained in a drying apparatus and used to aid in controlling the operation of the dryer. The detector head (102) is mounted to a traversing beam (105) and the detector head (102) is capable of traveling to positions across the width of the material being processed.

12 Claims, 5 Drawing Sheets

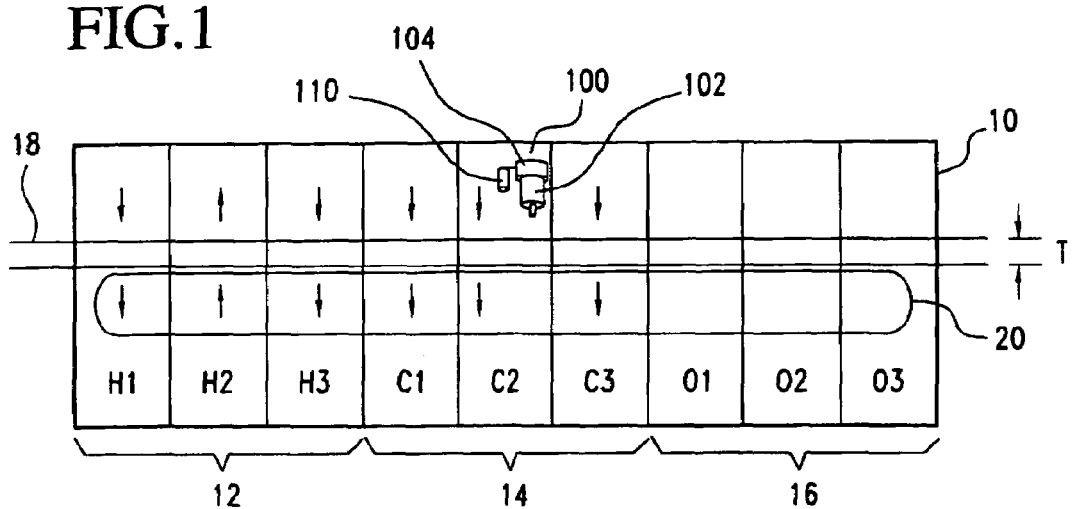
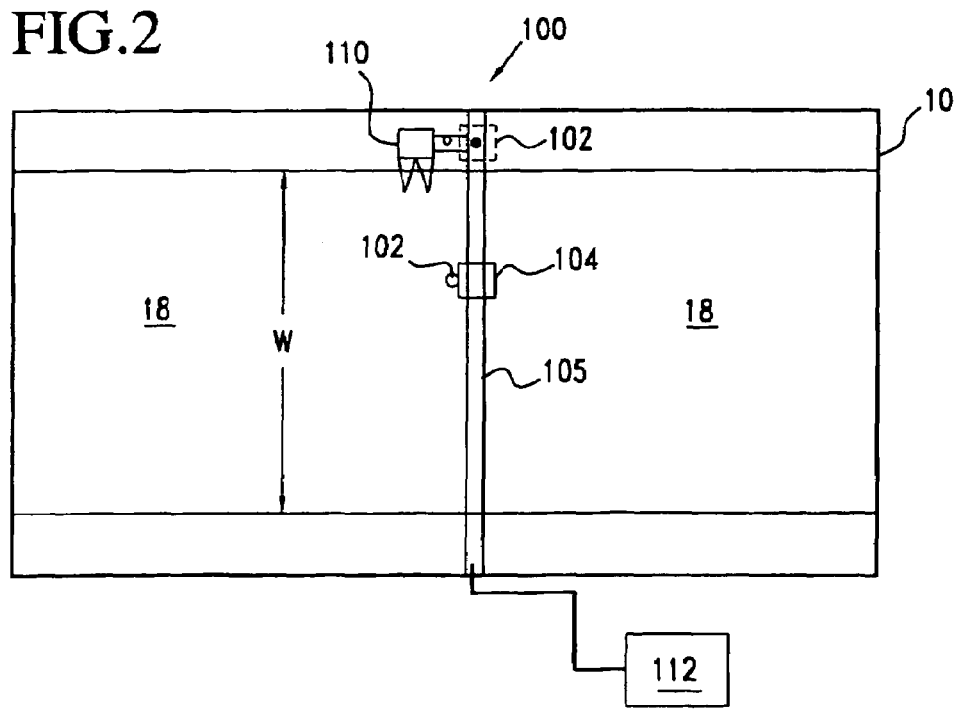

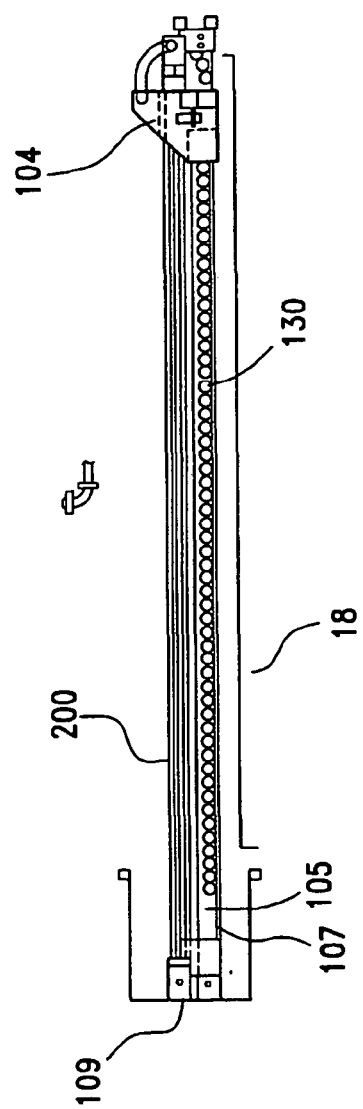
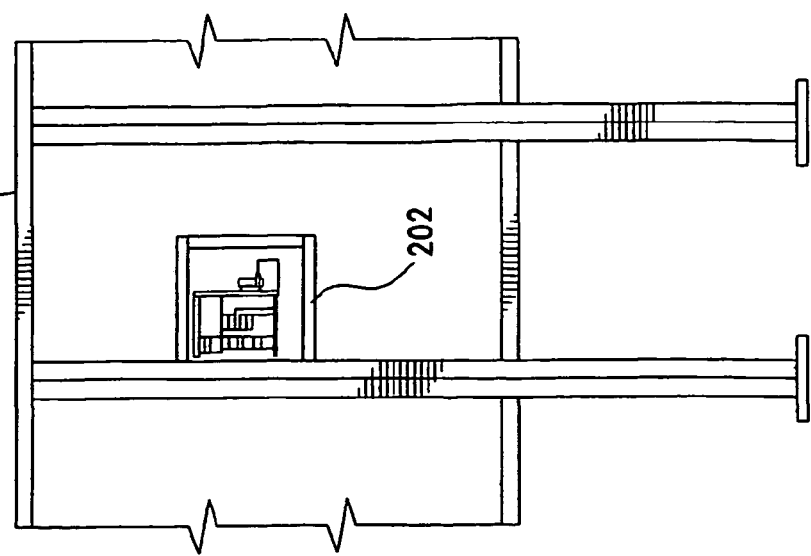
FIG. 3
FIG. 4

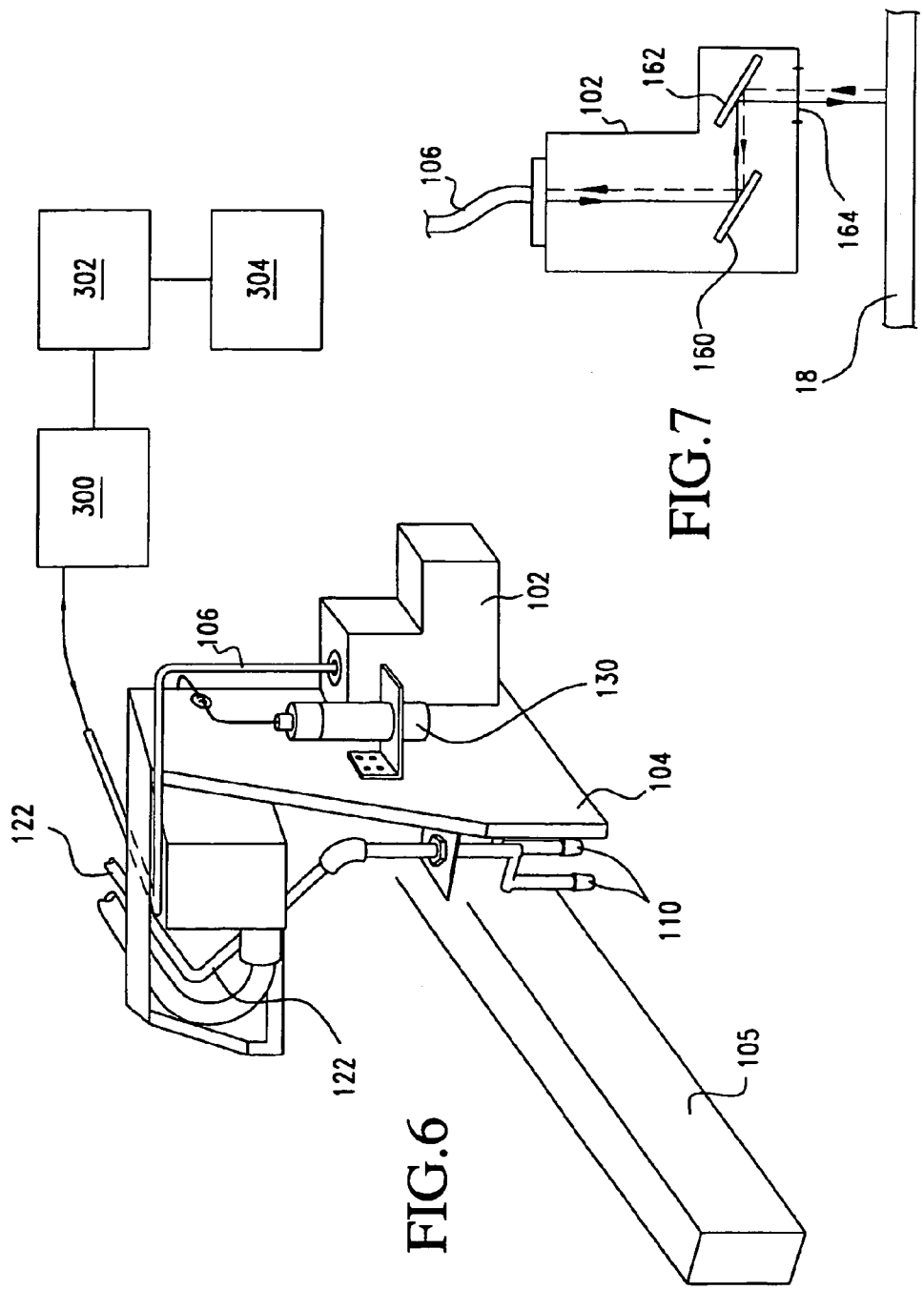

TRAVERSING MEASUREMENT SYSTEM FOR A DRYER AND ASSOCIATED METHOD

BACKGROUND OF THE INVENTION

1. Field of the Invention

This invention is directed to a system and method for obtaining measurements across the width of a material being dried in an industrial dryer.

2. Description of Related Art

Industrial dryers are used, for example, in drying tobacco in various processed forms prior to the tobacco being used in producing finished products. Other products also require drying as part of the processing to produce the final product. In certain tobacco drying processes, for example, an "apron", or substantially continuous moving sheet, of tobacco in semi-processed condition is passed through dryer units at one or more stages prior to packaging for shipment to a tobacco products manufacturer. The tobacco is checked for moisture content after it has been processed through the dryer, in order to determine whether the moisture level of the tobacco is at or below the maximum moisture level as dictated by the tobacco products manufacturer. If the moisture level exceeds the maximum level imposed, the tobacco must be reprocessed at great expense to the supplier, in order to be sold to the tobacco products manufacturer.

Similar scenarios are present in a variety of industries outside the area of tobacco production, in which the moisture content or other properties of the intermediary product must meet specifications dictated by the purchaser of the intermediary product. In such instances where moisture content is measured only at the completion of processing, the same situation can arise that the intermediary product must be further processed in order to be accepted by the purchaser.

Moisture control in apron style tobacco dryers has long been a challenge to the industry. This is due to the fact different tobaccos and tobacco blends have varying densities, as well as percentages of casing, affecting the tobacco carpet depth and/or mass flow throughput. The leaf stalk position and the environmental conditions at the time of processing also contribute to changes in the drying process. These changes represent more or less work/energy transfer required to achieve the desired results. This causes the operator to adjust both heating (drying) and re-ordering (moisturizing) zones of this multiple stage process. Most tobacco processing lines have dryers with three or more zones of heating, one or more zones of cooling, and two or more zones of re-ordering.

Processing originally depended entirely on the acquired skill of the operator's hand to determine the approximate moisture content of the tobacco discharging from the dryer. With the reduction of cost for a standard on-line moisture gauge to less than $10K per unit, many dryers are now fitted with moisture gauges at the discharge to assist operators in monitoring the quality of the product exiting the dryer. To date, most operations have relied on this final moisture value supported by lab results, in conjunction with measured internal dryer temperatures, to make necessary adjustments to control the process.

Recently, with the need to achieve the highest production rates possible with existing equipment and ever tightening customer product quality control standards, tobacco processors have been looking for a method to better control the drying process and reduce standard deviation. One major problem has been that the drying process is both multiple zone and bi-directional. Therefore, no reliable means for determining the average moisture after drying and before re-ordering was readily available. Some processors have placed standard on-line moisture gauges inside the cooling sections of dryers with limited success. Mainly because it is a single point-measuring device mounted at a fixed position along the longitudinal axis of an apron style dryer, the data does not provide a true profile of the product across the entire dryer width and therefore is of limited use. This is further complicated by the fact standard photometers (moisture gauges) in this environment are operating near or at their maximum operating temperature, affecting both their performance and life cycle (MTBF).

It is therefore a principal object of the present invention to provide a system and method for taking measurements of, for example, moisture levels present in a moving product stream, and employing that information to aid in determining whether the product will meet moisture level requirements imposed by a purchaser of the product.

It is a further principal object of the present invention to provide a system and method for taking measurements of, for example, moisture levels present in a moving product stream, and employing that information in a control loop or control scheme for controlling process equipment used to produce the desired product.

It is a further principal object to provide a system for measuring particular properties of a material being processed in an enclosed area, which deploys a compact detector head within the enclosed area, and which delivers an NIR reflected energy to an electronics package external to the enclosed area for processing.

SUMMARY OF THE INVENTION

The above and other objects of the present invention are achieved by providing a fiber-optic based property measurement system which is operable to detect near-infrared (NIR) energy in a product traveling past a fiber-optic detector head, and in which the NIR energy detected can be correlated to a property or properties of the traveling product. The measurement system employs a bracket or "traverse beam", across which the fiber optic head is driven, so as to permit measurements to be taken at various positions across the width of a product stream.

The fiber optic based measurement system provides a non-contact detection system which thus performs the measurements non-destructively. The system, which is made up of the fiber optic head, the traverse beam, the means for driving the fiber-optic head across the traverse, and the other associated parts and components, provides a very compact detector unit, which is thus capable of being installed within various types of processing equipment, thereby permitting in situ measurements to be taken and used in any manner desired, for example, as feedback information to an equipment controller.

It was determined that, if a reliable measurement could be made in the cooling section, the operator could control the heating zones to prevent overdrying the tobacco. Since the smoking flavor and degradation of the product are both linked to the drying process, this is viewed as an important step towards improving process control and product quality. The measurement system developed as an aspect of this invention uses a NIR fiber optic cable and remote probe mounted on a linear traverse to allow the NIR electronics to be located outside of the dryer and also allow the measurement of the surface moisture across the entire apron width, providing a true average surface moisture value as well as defining the drying profile. The profiles provided can be used to adjust product in-feed sweep speed and/or energy distribution to reduce any unnecessary induced moisture deviation from the average value.

The system measures process variables/constituents on a continuous basis and collects data at specified (customer or otherwise) positions across the entire apron width. To improve repeatability, single measurement electronics is provided for each process variable (PV). The data is displayed in actual engineering units through a color touch screen display mounted in the control cabinet provided or optionally mounted up to 150' away from the control cabinet. The system is designed to automatically trend collected data with reference to real time and develops dryer profile bar charts that are updated regularly. From the visual graphics provided, the dryer performance can be quickly reviewed so corrective action can be made. This allows improvement of the dryer's final product output consistency; thereby reducing standard deviation of the final product. In addition, the system provides real time measurements of process variables for use in both feedback and feed forward control loops providing optimum dryer performance and maximum return on investment.

The system design can preferably include measurements such as tobacco carpet surface moisture, product temperature, bed depth and cooling section ambient air temperature measurements, as well as the ability to measure inner core moisture and temperature. Relative humidity measurements can also be provided if desired. Operator input fields are provided on an input screen for entry of product identification and target moisture value. From the trending/chart menu selection on the interface, the real time and historical data can be reviewed in the form of trend lines and bar charts. Due to a finite electronic data storage capacity of the system, new data will, at some point, overwrite the oldest data on the flash memory card. The system also allows for the continuous archiving of data to a CSV file located on a PC via 10/100 Ethernet network.

The system includes the ability of the sensor to return to a home position, which is preferably in an enclosure positioned flanking the side wall of the process equipment, thus providing access to the sensor carrier for periodic maintenance and validation. The enclosure is mounted to the vertical dryer frame member on the door closure (latch) side. The traverse assembly requires an approximate 20" square door cutout and a 24" high clearance above the apron. This measurement system would also traverse the entire width to provide average and profile data for both product moisture and temperature.

The electronics package that traditionally has been provided in the same housing as the NIR optical detector components is, in the present system, disposed at the exterior of the processing equipment, and the NIR optical detector components and associated processing electronics are optically coupled by a flexible fiber-optic cable which extends from the NIR optical detector inside the processing equipment to an electronics package mounted at the exterior of the equipment. This allows the use of a much more compact detector head inside the processing equipment.

The system of the invention further optionally includes a blower or agitator which can be intermittently used to temporarily or permanently remove an outer surface or layer of the product being processed, so that the properties of the product material below the outer surface may be detected by the fiber optic head. Thus, for example, in a product dryer, in which an exposed surface of the product may be dried to a greater degree than the underlying material, a more accurate measurement of the overall moisture level in the product may be obtained.

BRIEF DESCRIPTION OF THE DRAWINGS

The above and other features of the present invention will be more readily understood from a reading of the ensuring detailed description of the preferred embodiment of the invention, taken in conjunction with the accompanying drawings, in which:

FIG. 1 is a substantially schematic side view of a preferred embodiment of the present invention as installed in an apron dryer employed to dry tobacco intermediary products.

FIG. 2 is a substantially schematic top view of the apron dryer of FIG. 1, showing the measurement system according to a preferred embodiment of the present invention installed therein.

FIG. 3 is a front elevation view of the general arrangement of the system mounted in a tobacco dryer.

FIG. 4 is a side elevation view of the general arrangement of the system, as viewed from the exterior of the tobacco dryer.

FIG. 6 is a perspective view of the traverse beam and associated components in accordance with a preferred embodiment of the present invention.

FIG. 7 is a substantially schematic cutaway view of the detector head in accordance with a preferred embodiment of the present invention.

DETAILED DESCRIPTION OF THE PREFERRED EMBODIMENT

Figure 5:
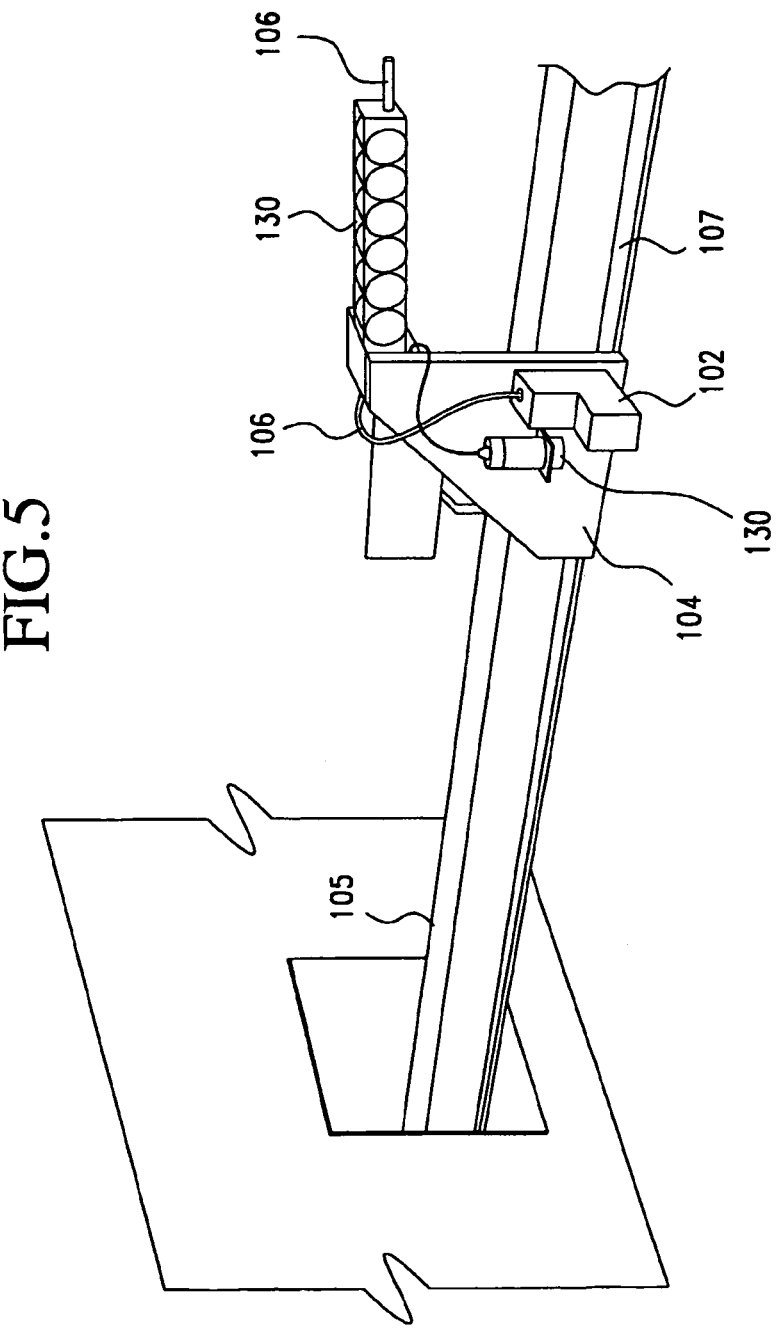
FIG. 5 is a perspective view of the carrier bracket and components mounted thereto, in accordance with a preferred embodiment of the present invention.
Figure 8:
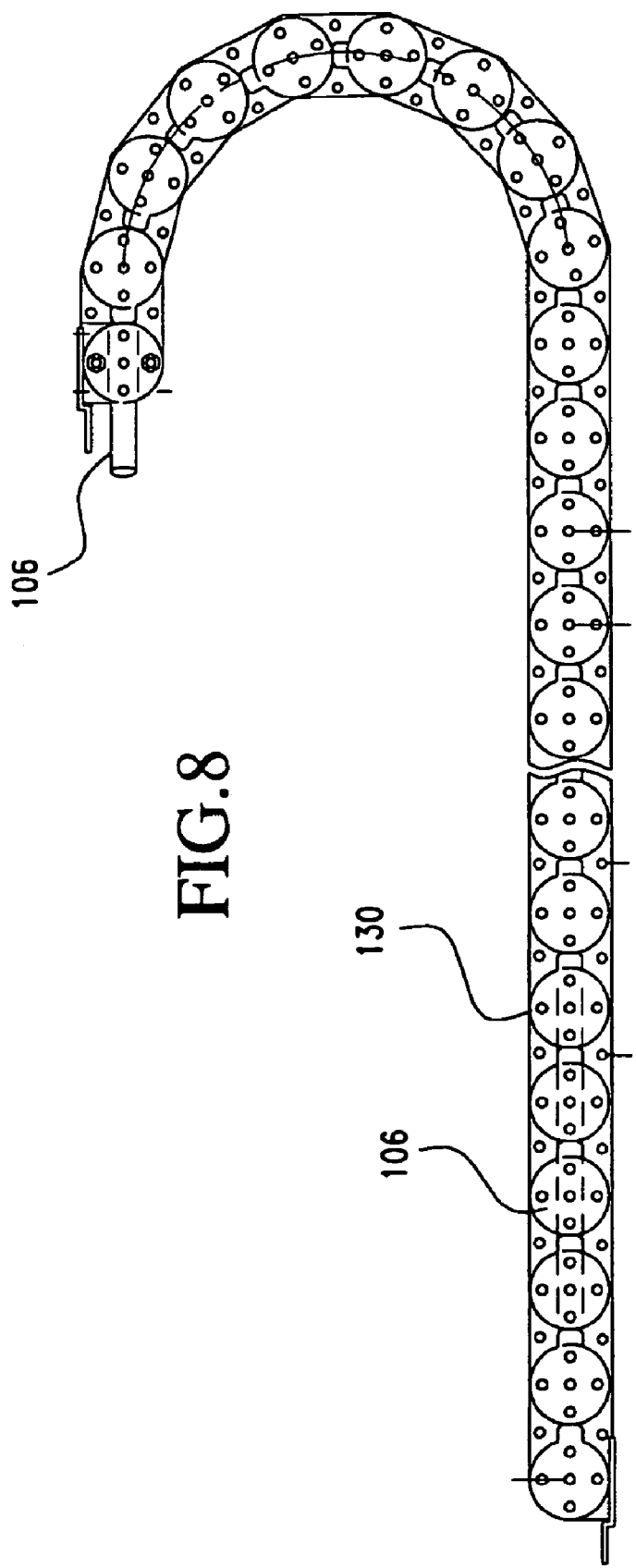
FIG. 8 is an enlarged view of the fiber optic cable carrier illustrated in FIG. 3.

Referring initially to FIGS. 1 and 2, a measurement system 100 is shown in schematic form as installed internally in what is referred to in the tobacco processing industry as an apron dryer 10. It is to be noted that the discussion of the invention as used in connection with an apron dryer, and in connection with the drying of tobacco, is solely for illustrative purposes, as the measurement system can readily be incorporated into any number of types of processing equipment, and is suitable for use in any applications in which a product properly or properties can be correlated to the emanation/reflection from the product of near-infrared (NIR) energy.

As other examples in the processing of tobacco, near-infrared energy reflected from the surface of the tobacco product can be used to determine the nicotine content of the tobacco, the sugar content, and/or the fat content, as well as other properties. A signature reflected energy pattern can readily be developed for each of these properties, as well as for other properties. When any or all of these other properties are determined to be of interest, the apparatus and method can readily be equipped or programmed, in a manner that will be readily apparent to those of ordinary skill in the art, to interpret the NIR energy detected such that the desired information can be provided. In addition, the system and method can be used in the processing operations for other products.

The apron dryer 10 in FIGS. 1 and 2 is commonly used to dry a partially processed tobacco product known in the art as "thrashed tobacco", or tobacco leaves that have been destemmed. The specific details of the construction of the apron dryer, and its specific modes of operation, are well understood in the dryer art, and do not form a specific part of this invention. As relevant to the present invention, it is noted that the apron dryer 10 has three basic sections, a heating section 12, made up of three heating units H1, H2, H3, a cooling section 14, made up of three cooling units C1, C2, C3; and an "ordering" section 16, made up of three ordering units, O1, O2, O3.

In the heating section 12, heated air is blown across the apron 18 of tobacco, to drive off moisture. The apron 18 is a substantially continuously moving sheet made up of tobacco leaves, and generally will have a thickness T on the order of 2-4 inches, and a width W on the order of twelve (12) feet. Aprons may actually be processed in discrete lengths, such as on the order of 100 feet in length, but may be regarded as being of substantially indeterminate and continuous length for the purposes of this invention.

The heated air is blown through the thickness of the apron in opposing directions, as indicated by the arrows in FIG. 1, in order to attempt to achieve even drying through the thickness of the apron. The apron 18 travels on a belt 20, normally made of highly perforated metal, such that the heated air can travel through the apron 18 in both directions indicated.

The apron passes from the heating section 12 to cooling section 14, where unheated or chilled air is blown through the apron to cool the material to substantially ambient temperature, or some other desired temperature. From the cooling section, the apron passes into an ordering section, in which the tobacco in the apron has moisture added via the introduction of steam or water through nozzles disposed in these units O1, O2, and O3.

The reason that the thrashed tobacco is first dried and then remoisturized is that a certain moisture level in the dried product is desired, yet the moisture content prior to drying is unevenly distributed in the thrashed tobacco, in which excessive moisture may be retained in any remaining stems or in the thicker portions of the tobacco leaf. Excess concentrated moisture of this type leads to product storage problems, in that mildew and rot can develop in the product in such situations. Thus, the product is generally dried beyond the level necessary to remove concentrated moisture, and is remoisturized in a more evenly distributed reordering process step.

In the operation of apron dryers in the prior art, the moisture of the product exiting from the dryer is not measured as the process is taking place, but is later measured to determine if the product meets the moisture content standards of the customer for whom the semi-finished tobacco product is to be supplied. Product which does not meet the moisture content requirement must undergo further processing in order to be accepted by the customer.

The system and method of the present invention minimize the chances that product exiting the apron dryer will exceed maximum moisture levels imposed by customers, while, at the same time, allow the producer to process tobacco to have moisture levels close to such imposed maximums. This can increase the profitability of the process, in that tobacco in the semi-finished form is sold on a per pound basis, and, when the moisture content is at or near the imposed maximum, there is less actual tobacco leaf in each pound of the delivered product.

The system of the present invention achieves the objectives by performing an in situ measurement, in this case a moisture measurement, thereby enabling the apron dryer 10 to be controlled in a real time or near real time manner, such that the moisture content of the tobacco exiting the drier is as close as possible to a desired level. The desired level would generally be set with the intent of having the delivered product come close to, but not to exceed, the maximum imposed by the customer, and, at the same time, minimizing the chances of rejects due to excessive moisture content. The system also provides these measurements across the width of the tobacco apron, which information can be used to ensure consistency across the entire apron.

The measurement system 100 includes a fiber optic NIR detector head 102, which is capable of emitting NIR energy toward the surface of the tobacco apron 18, and receiving back a reflected NIR energy. The detector head 102 will be referred to herein as a "passive" optical head, in that the detector head will not process the reflected energy signal itself, but will merely serve as the front end of a conduit to an electronics package 300 located external to the dryer 10, where the detected NIR energy is to be processed. The detector head 102 is mounted on a bracket 104, and the bracket 104 is movingly mounted to a traverse beam 105. The traverse beam 105 is installed in the dryer to span essentially the entire width of the product, here, the apron of tobacco 18, which travels through the dryer. The fiber optic detector head 102 is coupled to a fiber optic cable 106 that is operable to transmit the detected NIR energy to a processor.

Fiber optic cable 106 may preferably comprise a bundle of optical fibers, for example, about 200 to 300 fibers, that are secured together to form a single "cable" having a combined diameter preferably in the range of about $\frac{1}{8}$-$\frac{1}{4}$ inch. Such a cable will be sufficiently flexible or pliant to be able to withstand the bending or deformation that the cable 106 will undergo as the detector head 102 traverses the width of the tobacco apron 18. The cable 106 is coupled to the detector head 102 in a manner such that the detected NIR energy will pass from the head/or into cable 106.

FIG. 7. shows, in substantially schematic form, a cutaway view of the detector head 102. It can be seen in this view that the detector head 102 houses a pair of mirrors 160, 162 and contains a lens 164 at a lower surface thereof. Fiber optic cable 106 is secured to an upper end of the detector head, and the bundle of optical fibers forming the fiber optic cable are oriented such that they are capable of delivering NIR energy essentially vertically downwardly into the interior of detector head 102 (see solid line representing NIR energy path). A first mirror 160 has a non-linear or non-planar mirrored surface which, as it is reflecting the NIR energy transmitted by the fiber optic cable 106, also conditions or focuses the incoming energy as desired. The energy is reflected at substantially 90°, to a horizontal path. A second mirror 162, reflects the energy again downwardly through a lens 164 disposed at the lower surface of the detector head 102.

The second mirror does not further condition the energy beam, but rather only reflects that energy. Similarly, the lens 164 is preferably neutral, meaning that it does not alter the energy beam in any significant way. The lens is provided principally to protect the interior of the detector head from the environment outside the detector head.

The NTR energy is thus directed downwardly toward the surface of interest, which, in the case of a tobacco dryer, is the traveling apron 18 of tobacco. The NIR energy is reflected off of the surface, with some absorption or diffraction occurring as a result of the condition and properties of the surface of interest. The reflected potion of the energy (see broken line path in FIG. 7) is received back through lens 164, and is directed back to fiber optic cable 106 by mirrors 162 and 160. The fiber optic cable 106 then channels the reflected energy to the programmable logic controller and attendant electronics 300 for analysis. A material property of interest, for example, moisture, may be determined based upon the characteristics of the reflected energy. Other material properties, such as sugar or nicotine content, or the like, may also be characterized in terms of reflected NIR energy, and the controller can be programmed to determine those other properties of the material/product under analysis, as well.

The construction of traversing bracket or beam 105 is generally known in the art, and may be used in connection with the present invention. A support tube 107, which may preferably be an aluminum tube of square or rectangular cross section, is preferably mounted by end supports 109 at either end of the tube 107. The end supports 109 may preferably be simple brackets having a box-shaped "U" which receives an end of the support tube therein. These end supports 109 are secured to the inner side walls of the process equipment, here, a tobacco dryer. An especially advantageous aspect of the detector head 102/traverse 105 combination employed in this invention is that it provides a very compact design which can be fitted into clearance spaces of as small as 24" from the top surface of the traveling product stream. The principal requirements of the traversing beam 105 are that the beam be sufficiently strong to support the detector head and attendant equipment above the product passing through below, including means for driving the detector head 102 and bracket 104 across the beam.

As the product travels past and underneath the detector head 102, detector head emits an NIR signal, and receives back a reflected NIR signal from the product. This information is then preferably transmitted through fiber optic cable 106, to a processor (discussed later) that is capable of correlating the reflected signal to a moisture content of a given product. Preferably, an IR sensor 130 is also provided, of a type that is commercially available, to measure temperature, as well.

Because dryers can dry a product unevenly across the width of the apron, the system of the present invention, which mounts the detector head 102 on a bracket 104, which in turn is mounted on traverse beam 105, is especially well-suited to obtain moisture measurements at various locations across the width of the apron. The traverse beam 105 is mounted transversely to the direction of product travel or flow. The traverse beam 105 is preferably equipped with means operable to move bracket 104 and detector head 102 across the beam. One preferred moving or driving means is a hydraulically operated linear actuator 200 mounted atop the beam 105. One such preferred linear actuator is the Precision Aire PSA-15, available from Tolo-matic, Inc., of Hamel, Minn.

The detector head control system 300 is preferably set up to control the linear actuator to stop the detector head at specific spaced-apart intervals across the width of the apron 18. The detector head will thus be able to take moisture and temperature measurements at desired points across the entire width, and will be able to detect any patterns of uneven drying from side-to-side on the apron of material. This data can be used to adjust the air blowers or the temperature of the air used in the heater section, or, possibly, such information might lead to the conclusion that the heating unit used to heat the air is malfunctioning and requires maintenance.

Another preferred, but optional, feature of the present invention is the provision of a pneumatic nozzle or nozzle array 110, which can be used to agitate or temporarily or permanently displace or remove a top layer of the product traveling past the detector head 102. In the case of using the system in an apron dryer, the nozzle 110 is carried by the bracket 104, which secures the detector head to the traverse such that the nozzle 110 is positioned at a fixed position relative to the detector head, at an upstream position therefrom. It is to be noted in FIG. 2, that the nozzle array 110 is shown connected to the broken line version of detector head 102, and the solid line version of detector head 102 is shown in a different position, for purposes of clarity of illustration.

The nozzle or nozzle array 110 is preferably oriented to blow air in a direction transverse to the direction of product flow or travel. In addition, the nozzle or nozzle array is preferably oriented at about a 45° angle from horizontal, or from the upper plane of the apron or carpet 18 of tobacco traveling past. Air blown through nozzle(s) 110 will, in the case of processing thrashed tobacco, temporarily lift one or more leaves from the surface of the apron, and may actually flip the one or several leaves off of the surface, in either case exposing product below the surface which may have a different moisture content than the product initially at the surface. Because the nozzle 110 is located immediately upstream of the detector head 102, the fiber optic NIR detector will be able to determine the moisture content, and the IR sensor, the temperature, of the product of a subsurface level. This is expected to further aid in characterizing the overall moisture content of the apron or carpet of tobacco, which, as noted previously, may be from about 2-4 inches in thickness. In turn, such information is expected to enable improved process control such that the final product will have the desired moisture properties, e.g., moisture content. The nozzle 110 will be connected to an external source of plant air or industrial air, by a hose 122 extending from the nozzle 110 to the exterior of the dryer or other equipment in which the system is installed.

The movement of fiber optic cable 106 is carefully controlled by cable guide 130. Cable guide 130 comprises a series of pivotable metal links, of, for example stainless steel or aluminum, with the adjacent links being connected to each other. The fiber optic cable is carried in the interior of this guide, between pins that span the spacing between opposing links. The cable guide is secured to bracket 104 adjacent the position at which fiber optic cable 106 is coupled to detector head 102, and is of a length approximately equal to the span of beam 105. The cable guide will pivot or fold back on itself as the bracket 104 travels from one end of the beam 105 toward the other end of the beam. The cable guide preferably maintains a predetermined radius of bending, such as about 6-9 inches, in order to prevent the optical fibers from being bent too severely, which could lead to breakage of the optical fibers.

The system will also preferably include a human/machine interface 112 that may include a screen display indicating date, time, traverse position, average moisture, average product temperature, measurement status, and manually entered product identification information, such as an identification number and a target moisture set point value. The system may optionally measure or monitor product parameters such as product (apron or carpet) height and ambient temperature.

The human/machine interface may include a graphing menu option, which, when selected, can present historical information such as:

a continuous graph of the average moisture/temperature or other constituents across the dryer width as a function of time, for the normal product surface, and/or the inner core surface;

a continuous graph showing values of the moisture deviation of the detected average moisture as compared against the target moisture set point value or other constituents across the dryer width as a function of time, for the normal product surface and/or the inner core surface;

a continuous graph of the moisture/temperature trend at any of the preset measurement locations across the dryer width as a function of time; and/or a bar chart of two-color bar graphs indicating, for each of the preset measurement locations across the width of the dryer, averaged moisture and temperature lines for the entire width for a selected time period during which continuous measurements were being made, showing the percentage deviation of moisture and temperature from the average shown on each bar graph.

The system further will preferably employ a programmable logic controller 300 that, in combination with the human/machine interface, will control the operation, calibration, data acquisition and analytical mathematical calculations for data archiving, for graphics, and to provide real time data, as the foundation for statistical process control. This set of electronics will preferably be mounted to an outside wall of the piece of process equipment, or be positioned at some remote location.

The controller will include standard components, known in the art of NIR sensors, that are capable of generating an NIR energy signal to be transmitted to and through fiber optic cable 106, and are capable of receiving and interpreting the NIR signal that is reflected back from the product being inspected, and channeled through the fiber optic cable. Once the NIR signal is interpreted, that information can be sent to a feedback or feed-forward controller 302, of a type known generally in the art, to be used in controlling the operation of the process equipment.

The provision of a human/machine interface 304 which can generate trend lines and profile (across the width of the apron) bar charts provides a significant tool for understanding the process taking place, by showing the inconsistencies in the process. The trend line information may be continuously updated, and the bar charts may preferably be updated on the order of every few minutes to show measured process variable deviation in the product in both the product feeds along the longitudinal axis of the dryer, as well as the drying process-induced gradient across the width of the dryer. Such data allows operational personnel to make adjustments in the operation of the dryer and to document the results of the adjustments immediately, thereby improving consistency and reducing standard deviation.

The process variable measurements may also preferably be used, as noted above, in either or both feedback or feed-forward control loops 302 to achieve optimum dryer performance.

While the illustrated embodiments provide an indication as to the preferred embodiment for carrying out this invention, it is to be understood that the true scope of this invention is set forth in the appended claims, and that variations from the preferred embodiments will fall within the scope of the appended claims.

What is claimed is:

1. A method for measuring a moisture level of a moving apron of tobacco in a tobacco dryer, comprising:
   (a) projecting a near-infrared (NIR) signal onto the moving apron of tobacco at a plurality of locations across a width of the moving apron by moving an NIR detector head to each of said plurality of locations;
   (b) receiving, in said NIR detector head, a reflected NIR signal, at each of said plurality of locations;
   (c) transmitting said reflected NIR signal through a fiber-optic cable, to a signal processing electronics package disposed exteriorly of the tobacco dryer; and
   (d) processing said signal in said electronics package to determine a moisture level at each of said plurality of locations.

2. A method as set forth in claim 1, further comprising displaying information in visible form which is representative of the moisture level determined at each of said plurality of locations.

3. A method as set forth in claim 1, further comprising employing said moisture level determination at said plurality of locations in a process control loop to control said tobacco dryer.

4. A method as set forth in claim 3, further comprising repeating steps (a)-(d) periodically, and employing said periodically obtained moisture level determinations in said process control loop.

5. A method for measuring at least one physical property of a moving product being processed in a dryer, said product being of indeterminate length, the process comprising:
   (a) projecting a near-infrared (NIR) signal onto the moving product at a plurality of locations across a width of the moving product in said dryer by moving an NIR detector head to each of said plurality of locations;
   (b) receiving, in said NIR detector head, a reflected NIR signal, at each of said plurality of locations;
   (c) transmitting said reflected NIR signal through a fiber-optic cable, to a signal processing electronics package disposed exteriorly of said dryer; and
   (c) processing said signal in said electronics package to determine said at least one physical property at each of said plurality of locations.

6. A method as set forth in claim 5, further comprising displaying information in visible form which is representative of the at least one physical property determined at each of said plurality of locations.

7. A method as set forth in claim 5, further comprising employing said physical property determination at said plurality of locations in a process control loop to control said method.

8. A method as set forth in claim 7, further comprising repeating steps (a)-(d) periodically, and employing said periodically obtained physical property determinations in said process control loop.

9. Apparatus for obtaining measurements of at least one property in a substantially continuously traveling product stream comprising:
   a detector head for transmitting and receiving a near-infrared (NIR) signal generated by a remote electronics package, said detector head being mounted on a bracket;
   a traversing beam extending transversely across an entire width of said continuously traveling product stream, said traversing beam having said bracket mounted thereon, said bracket being movably mounted to said traversing beam;
   means for transporting the bracket across a width of said traversing beam, said transporting means being capable of stopping said bracket at a substantially continuous range of positions across said width;

a fiber optic cable operatively coupled to said detector head and extending to a position physically remote from said traversing beam and said detector head; an electronics package coupled to said fiber-optic cable at said physically remote position, said electronics package including means for generating an NIR signal and for emitting said NIR signal to and through said fiber-optic cable, said electronics package further including means for receiving reflected NIR signals from said fiber-optic cable, and means for processing said reflected NIR signals to determine at least one property of said product stream corresponding to said reflected NIR signal detected at a particular position on said traveling product stream.

10. A method for measuring a moisture level of a moving apron of tobacco in a tobacco dryer, comprising:
   (a) projecting a near-infrared (NIR) signal onto the moving apron of tobacco at a plurality of locations across a width of the moving apron by moving an NIR detector head to each of said plurality of locations;
   (b) receiving, in said NIR detector head, a reflected NIR signal, at each of said plurality of locations;
   (c) transmitting said reflected NIR signal to a signal processing electronics package;
   (d) processing said signal in said electronics package to determine a moisture level at each of said plurality of locations, and
   (e) employing said moisture level determinations at said plurality of locations in a process control loop to control said tobacco dryer.

11. A method as set forth in claim 10, further comprising repeating steps (a)-(d) periodically, and employing said periodically obtained moisture level determinations in said process control loop.

12. Apparatus for obtaining moisture measurements in a substantially continuously traveling tobacco product stream in a tobacco dryer comprising:

a detector head for transmitting and receiving a near-infrared (NIR) signal, said detector head being mounted on a bracket;

a traversing beam extending transversely across an entire width of said continuously traveling tobacco product stream, in said tobacco dryer, said traversing beam having said bracket mounted thereon, said bracket being movably mounted to said traversing beam;

means for transporting the bracket across a width of said traversing beam, said transporting means being capable of stopping said bracket at a substantially continuous range of positions across said width;

a fiber optic cable operatively coupled to said detector head and extending to a position physically remote from said traversing beam and said detector head;

an electronics package coupled to said fiber-optic cable at said physically remote position, said electronics package including means for generating an NIR signal and for emitting said NIR signal to and through said fiber-optic cable, said electronics package further including means for receiving reflected NIR signals from said fiber-optic cable, and means for processing said reflected NIR signals to determine at least one property of said product stream corresponding to said reflected NIR signal detected at a particular position on said traveling product stream.

* * * * *